(12) United States Patent
Tennant

(10) Patent No.: US 11,730,973 B2
(45) Date of Patent: Aug. 22, 2023

(54) METHODS AND APPARATUS FOR LIGHT THERAPY TREATMENT OF MEDICAL AILMENTS

(71) Applicant: Tennant Systems, LLC, Austin, TX (US)

(72) Inventor: Jared Lane Tennant, Austin, TX (US)

(73) Assignee: Tennant Systems, LLC, Austin, TX (US)

( * ) Notice: Subject to any disclaimer, the term of this patent is extended or adjusted under 35 U.S.C. 154(b) by 218 days.

(21) Appl. No.: 17/373,401

(22) Filed: Jul. 12, 2021

(65) Prior Publication Data
US 2023/0011868 A1    Jan. 12, 2023

(51) Int. Cl.
*A61N 5/06*    (2006.01)

(52) U.S. Cl.
CPC .... *A61N 5/0613* (2013.01); *A61N 2005/0631* (2013.01); *A61N 2005/0632* (2013.01); *A61N 2005/0651* (2013.01)

(58) Field of Classification Search
CPC ........ A61N 5/06; A61F 9/00; A61F 2009/008
See application file for complete search history.

(56) References Cited

U.S. PATENT DOCUMENTS

2013/0226270 A1    8/2013    Tennant

*Primary Examiner* — Lynsey C Eiseman
(74) *Attorney, Agent, or Firm* — FisherBroyles LLP; Theodore Naccarella

(57) ABSTRACT

The disclosure pertains to biotransducers and particularly to methods and apparatus for treating medical conditions and ailments using light therapy biotransducers.

17 Claims, 6 Drawing Sheets

METHODS AND APPARATUS FOR LIGHT THERAPY TREATMENT OF MEDICAL AILMENTS

FIELD

This disclosure pertains to biotransducers, and particularly to methods and apparatus for treating medical conditions and ailments using light therapy biotransducers.

BACKGROUND

U.S Published Patent Application 2013/0226270, incorporated fully herein by reference, discloses a biotransducer and associated methods and apparatus for use in treating macular degeneration and other medical conditions using the piezoelectric effect.

Piezoelectricity is a charge that accumulates in certain solid materials (such as crystals and certain ceramics) in response to applied mechanical stress. Conversely, materials exhibiting the direct piezoelectric effect (the internal generation of electrical charge resulting from an applied mechanical force) also exhibit the converse piezoelectric effect (the internal generation of a mechanical strain resulting from an applied electrical field). Thus, when a piezoelectric material is properly cut and mounted, it can be made to distort in response to an electric field by applying a voltage to an electrode near or on the piezoelectric material. When the field is removed, the material generates an electric field as it returns to its previous shape, and this can generate a voltage. More broadly, a piezoelectric material can be caused to variably distort and/or variably generate a voltage in response to a changing electromagnetic field.

U.S Published Patent Application 2013/0226270 discloses a system in which a piezoelectric oscillator, such as a crystal, is coupled in parallel with an inductor to create a resonant circuit in which the oscillator takes the place of a capacitor in a typical LC resonant circuit, creating a modified LC-type circuit. More particularly, a power supply provides a voltage to the modified LC-type circuit to activate the piezoelectric effect in the oscillator by electrical distortion (rather than mechanical distortion). The resulting effect is an electromagnetic field having characteristics depending on the particular piezoelectric material and inductor impedance.

One or more light emitting diodes (LEDs) that generate light at one or more desired wavelengths are configured to receive an output of the modified LC-type circuit.

A frequency generator is also coupled to the modified LC-type circuit. The frequency generator is adapted to apply one or more electrical signal patterns (e.g., frequency sets) to the modified LC-type circuit to modulate the frequency sets onto the output of the LC-type circuit, thereby modulating the output of the LEDs.

The frequency generator is configured to generate an electrical signal pattern to modulate the resonant circuit with a pattern to create an electromagnetic field having a particular therapeutic effect, the electrical signal pattern and its therapeutic effect being particular to the specific medical condition being treated and/or therapeutic effect desired.

The signal from the frequency generator alters the capacitance and/or an inductance of the resonant circuit and the light from the LED(s) that is affected by the electromagnetic field can be applied to a body part to adjust a pH of cells in the tissue.

BRIEF DESCRIPTION OF THE DRAWINGS

A more detailed understanding may be had from the detailed description below, given by way of example in conjunction with the drawings appended hereto. Figures in such drawings, like the detailed description, are exemplary. As such, the Figures and the detailed description are not to be considered limiting, and other equally effective examples are possible and likely. Furthermore, like reference numerals ("ref.") in the Figures ("FIGS.") indicate like elements, and wherein.

SUMMARY

Figure 1A:
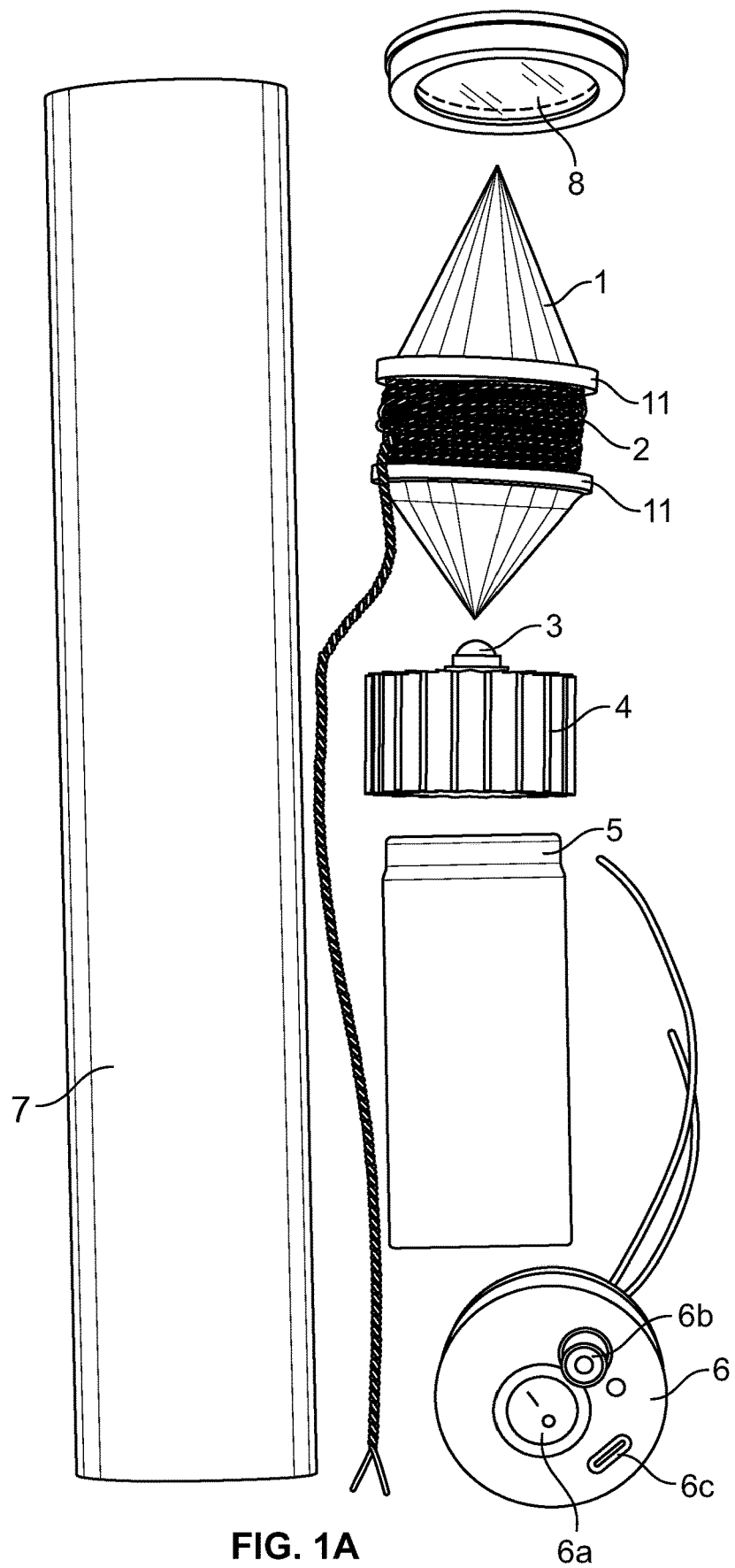
FIG. 1A is a pictorial representation of the components of a biotransducer in accordance with an embodiment.

Disclosed is a biotransducer for treating medical ailments comprising a resonant circuit comprising an inductor and a piezoelectric crystal and a light source for producing illumination, wherein the light source is positioned relative to the resonant circuit such that illumination emanating from the light source passes through an electromagnetic field of the resonant circuit, wherein the piezoelectric crystal comprises a unitary body having a first longitudinal segment at a first end thereof, a second longitudinal segment in the middle thereof, and a third longitudinal segment at a second end thereof, wherein the second longitudinal segment is cylindrical, the first longitudinal segment is tapered away from the second longitudinal segment to a first point, and the third longitudinal segment is tapered away from the second longitudinal segment to a second point, wherein the light source is positioned relative to the resonant circuit such that illumination emanating from the light source passes through an electromagnetic field of the resonant circuit from the direction of the first point to the second point of the piezoelectric crystal.

Also disclosed are methods for treating medical ailments using the biotransducer.

DETAILED DESCRIPTION

A living body maintains and heals itself by making new cells. Certain illnesses may occur when the body loses its ability to generate new cells that work correctly. Furthermore, cells only function normally in an environment having the correct pH. For example, certain cells function optimally at a pH of about 7.35 to about 7.45.

While pH is commonly considered to be a measurement of the acidity or alkalinity of a solution, in which a pH of 7 is neutral, and measurements lower than 7 (down to 0) indicate increasing acidity and measurements higher than 7 (up to 14) indicate increasing alkalinity, pH level is actually a measurement hydrogen ion concentration of the solution, and thus is, in essence a measurement of voltage. Voltage in a solution may be in the form of an electron donor or an electron acceptor. If the voltage of a solution is positive, then that solution is an electron acceptor. If the voltage of a solution is negative, then that solution is an electron donor. In a pH measurement, the measured voltage of a solution is converted to a logarithmic scale between 0 and 14. For instance, a pH value of 7.35 is equivalent to −20 millivolts, i.e., a week electron donor. A pH value of 7.45 is equivalent to −25 millivolts, i.e., a slightly stronger electron donor.

In order for certain cells to effectively regenerate in a living body, they may require a certain pH or pH range (i.e., voltage or voltage range, such as about −50 millivolts). When cells lose their voltage, they may not only lose their ability to function property, they may also lose the ability regenerate (generate new cells). If cells begin to malfunction and/or lose or diminish their ability to replace themselves with new cells that have adequate voltage and function properly, it can lead to certain chronic diseases. For example, as the voltage in cells drops, oxygen levels drop because the amount of oxygen that dissolves in a solution is dictated by the voltage of the solution. For instance, macular degeneration occurs when the voltage of the cells is too low for the cells to function normally and/or to regenerate themselves with cells that function properly. Thus, pH (voltage) is a cause (possibly the primary cause) of certain chronic diseases, including macular degeneration. Clinical experience has shown that when the voltage is corrected in the macula, vision can be restored.

Herein is disclosed a new and improved biotransducer that can adjust the pH (voltage) of cells, such as in the retina, in order to help promote healing.

As discussed above, US Published Patent Application No. 2013/0226270 discloses a method and apparatus including a system for treating medical ailments using the principles discussed above, namely, adjusting the voltage of cells to optimal levels for improving cellular functionality and/or regeneration. By controlling a frequency generator to apply particular frequency patterns to a resonant circuit, which in turn cause light from a light source to pulsate in certain patterns, an electromagnetic field of therapeutic effect is generated that can be applied to a living body for curative purposes.

Figure 1B:
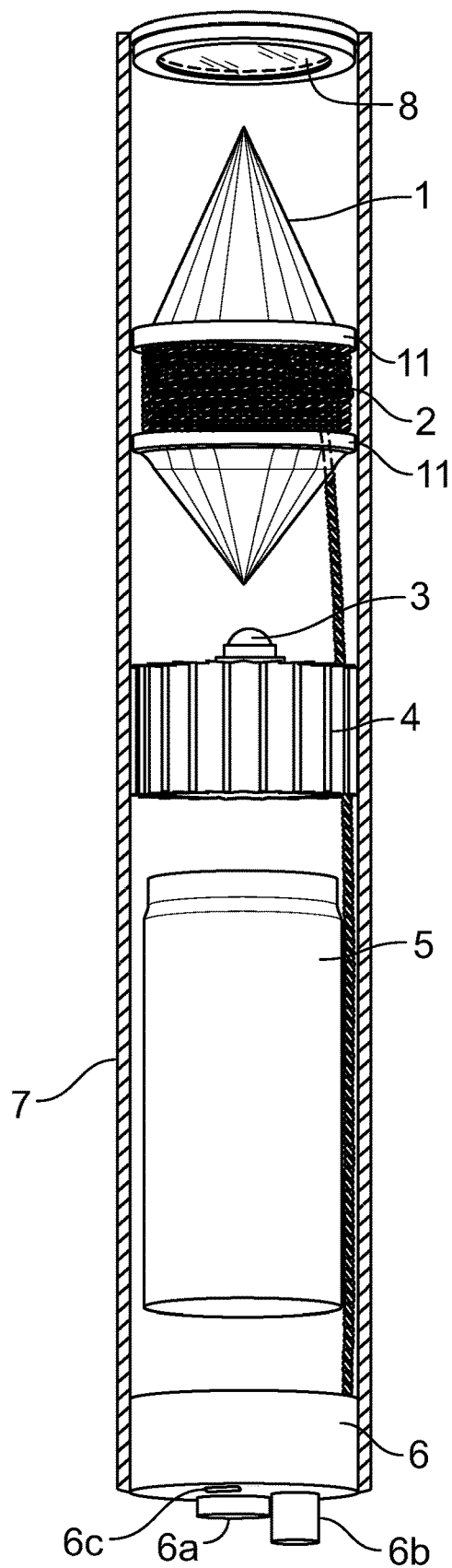
FIG. 1B is a cutaway assembly view of the assembled biotransducer.
Figure 2:
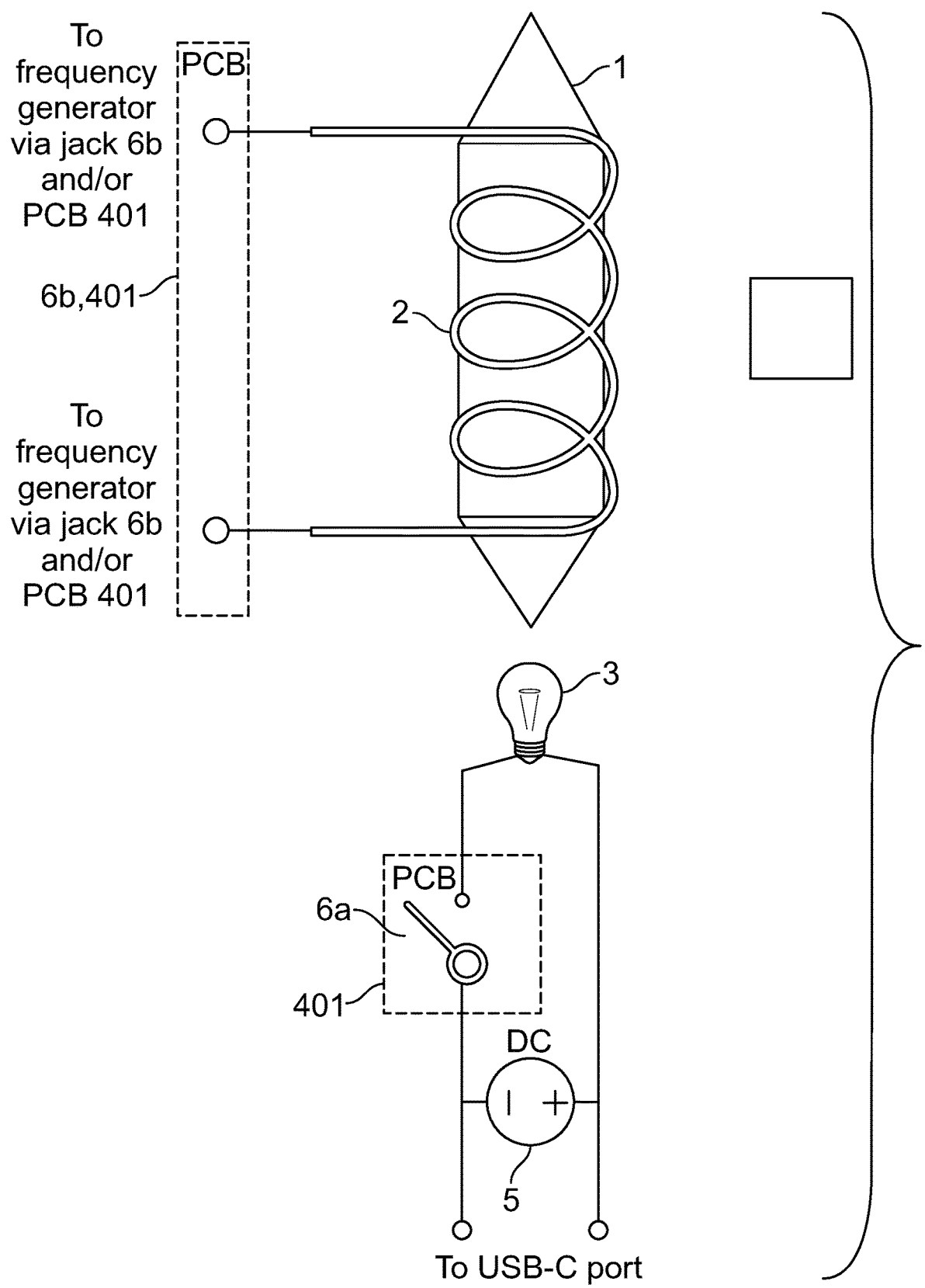
FIG. 2 is a circuit diagram of the electrical components of the biotransducer shown in FIG. 1 in accordance with an embodiment.

FIGS. 1 and 2 are, respectively, a pictorial diagram and a circuit diagram of the components of an improved biotransducer in accordance with one preferred embodiment.

The biotransducer comprises a light source, such as a Light Emitting Diode (LED) 3. In one embodiment, the LED is a 1 watt LED that emits light in the photo red range. e.g., 660 nm wavelength. The light source, including its power, magnitude, and/or wavelength may be altered to suit the particular therapeutic need. The light source is powered by a suitable power source, such as a battery 5. In one embodiment, the battery is a 32700 lithium iron phosphate (LeFEPo4) battery of 6000 mah (milliampere hours). The light output by the light source is passed through a piezoelectric resonator circuit, which may comprise a piezoelectric oscillator, such as crystal 1, surrounded by an electrical wire (coil).

Figure 3B:
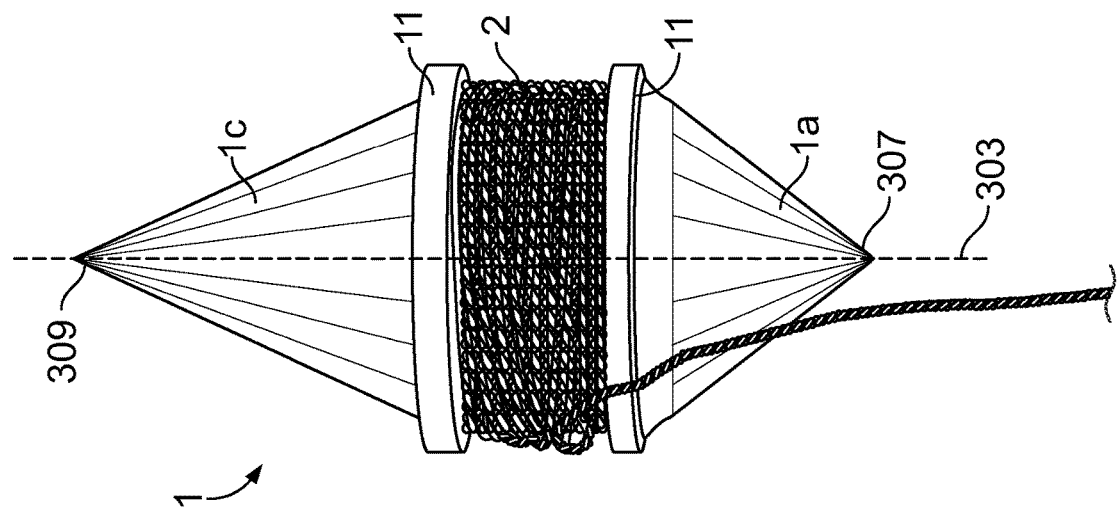
FIG. 3B is a more detailed pictorial depiction of the crystal oscillator and inductor coil of FIGS. 1 and 2 in accordance with an embodiment.
Figure 3A:
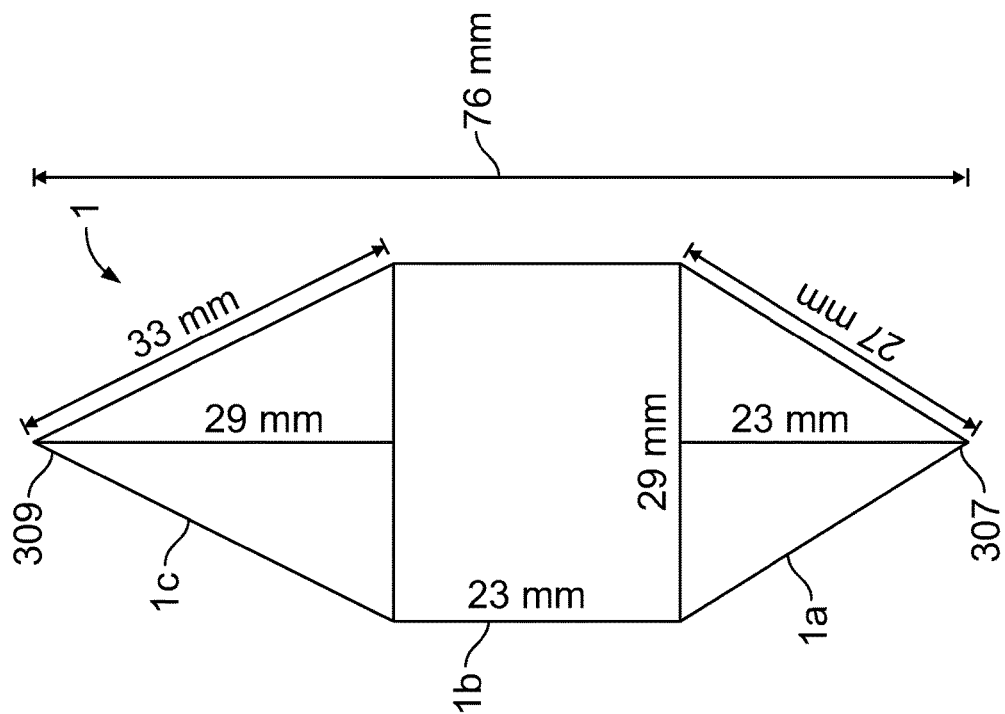
FIG. 3A is a more detailed, dimensional drawing of the crystal oscillator of FIGS. 1 and 2 in accordance with an embodiment.

Referring to FIGS. 3A and 3B, which are a dimensional drawing or an exemplary crystal 1 and a pictorial drawing of the crystal 1 and including the inductor coil 2, respectively, in a preferred embodiment, the crystal 1 is a 24 sided quartz crystal having the dimensions shown in FIG. 3A. The crystal may be of any piezoelectric crystal composition. In a preferred embodiment the crystal is clear quartz and may be hand carved. Particularly, for explanatory purposes, while the crystal 1 is a single unitary piece, it may be considered to comprise three different longitudinal segments, namely, an input segment 1a, a middle segment 1b, and an output segment 1c. The entire crystal, including all three sections, has 24 facets arranged around its longitudinal axis 303.

The middle segment 1b is generally cylindrical, i.e., the facets are parallel to each other, but, of course, is not literally cylindrical as the side wall comprises 24 generally flat facets rather than the continuously curved surface of a true cylinder.

The input and output segments 1a and 1c, however, are tapered inwardly to points as one moves away from the middle section 1b. Thus, the 24 facets meet at a first point 307 at the input longitudinal end of the crystal 1 and again at a second point 309 at the output longitudinal end of the crystal. In a preferred embodiment, the input segment is tapered at an angle of 63 degrees, while the output end is tapered at an angle of 54 degrees, which angles have been determined to have a particularly beneficial therapeutic effect.

In a preferred embodiment, for particular therapeutic value, the crystal may be 76 mm in length, with the input section being 27 mm long, the middle section being 29 mm long, and the output section being 33 mm long. The diameter of the middle section is 29 mm (as measured from the edge of a facet to the edge of an opposing facet.

An electrically conductive coil 2 encircles the middle segment 1b of the crystal. The coil is to be electrically coupled to receive a variable electrical voltage across its terminals from a carefully controlled frequency generator (not shown) to create a therapeutically useful electromagnetic field via the resonant circuit formed by the interaction of the charged coil 2 and the piezoelectric crystal 1.

In operation, the light emitted from the light source 3 is caused to pass through the electromagnetic field created by the resonant circuit formed by the coil/piezoelectric crystal combination, and is applied to the particular biological body or body part that is being treated.

In a preferred embodiment, the coil 2 is formed of a length of enamel coated copper wire that is folded in half upon itself and then twisted to cause the two halves to intertwine in a generally helical nature. In one preferred embodiment, the wire is twisted to create a 45 degree angle between the two halves of the wire as they wrap around each other. The 45 degree angle is therapeutically significant as it offers the maximum level of electrical interference.

In one example, the twisted wire may be formed by taking the desired length of wire, folding it in half, fixing one end of the doubled over wire (e.g., the end at which the wire is folded upon itself) so that it cannot rotate, applying sufficient tension to the wire to cause the entire length of the doubled over wire to be relatively straight, and then twisting the two halves of the wire over each other the appropriate number of turns. In an embodiment, the twisting may be accomplished by attaching the two free ends of the wire to a drill or other rotary tool (e.g., using an appropriate bit attachment that can hold the two wire ends) and operating the rotary tool to twist the wire.

Referring back to FIG. 1, the various electrical components of the biotransducer may be housed within a tubular housing 7. The housing may be formed of plastic, metal, carbon fiber, or any other suitable material. The housing may by cylindrical and may be 230 mm in length by 40 mm. the wall may be 1 mm thick, thus making the inner diameter of the tubular housing 38 mm. The housing includes an end cap 6. The endcap 6 may include a switch 6a electrically coupled to turn the device on and off, e.g., allow electricity to flow from the battery 5 to the LED 3 to cause the LED to light up. The endcap 6 also may include an electrical jack 6b, such as an RCA style two-terminal jack. The jack 6b may be adapted to couple to a cable connector from a frequency generator (not shown in the FIGS.) that generates the therapeutically effective electric signal patterns to be applied to the coil of the resonator circuit. Accordingly, the two ends of the inductor wire 2 would be coupled to the internal portions of the jack 6b so that the signals from the external frequency generator are applied to the coil.

The end cap may also include a port 6c, such as a USB-C port for charging the battery 5.

Of course, in other embodiments, the frequency generator may be unitary with the aforementioned biotransducer components, (e.g., may be contained within the housing 7), as opposed to being an external unit that is coupled via cable to the biotransducer.

Figure 4:
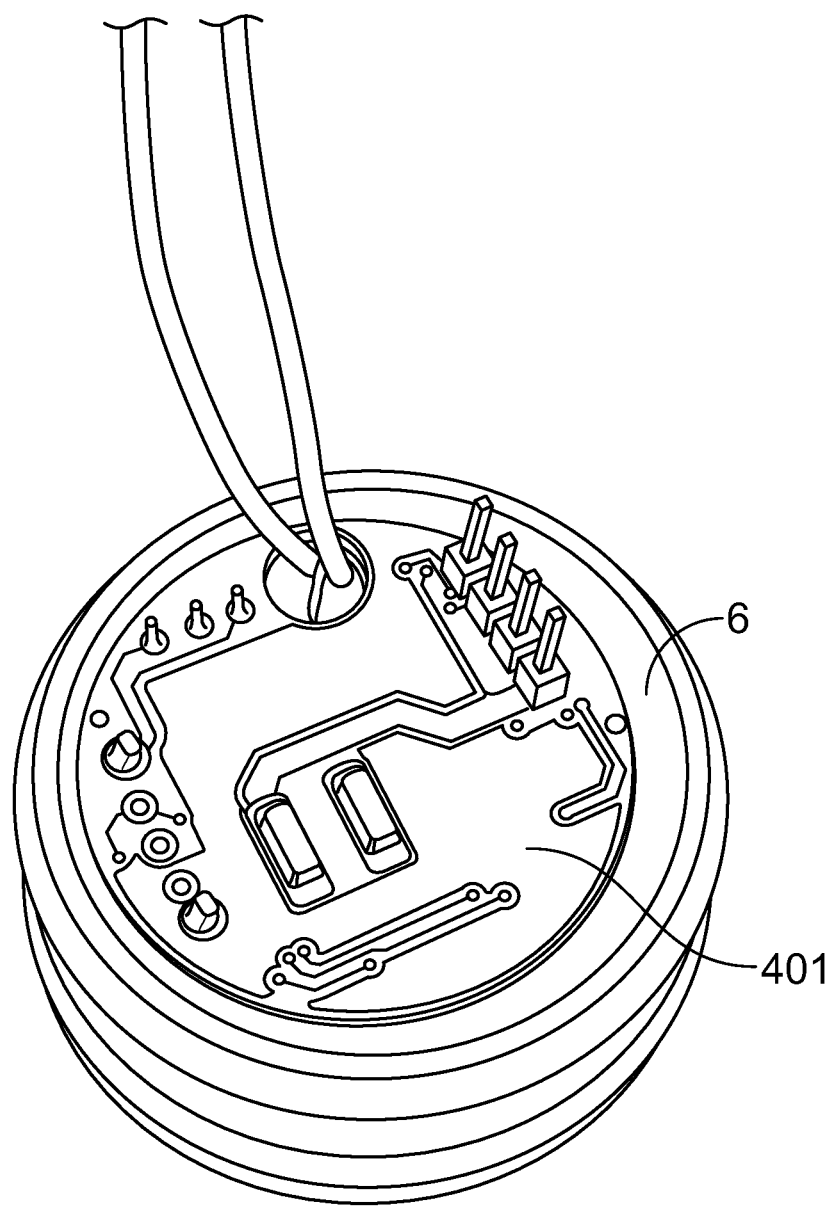
FIG. 4 shows the end cap of FIG. 1 in more detail, including a printed circuit board embedded in the end cap, in accordance with an embodiment

With reference to FIG. 4, the end cap 6 may be adapted to hold an appropriate printed circuit board (PCB) 401 designed to control the electrical components of the biotransducer. For instance, the PCB 401 may regulate the voltage from the battery to the appropriate voltage for the LED. For instance, in an embodiment, the PCB may regulate the voltage from a 5 volt battery to power the LED via constant current of 350 milliamperes at 2.2 volts. It also may include circuitry for the USB-C port, as well as the various electrical pathways for intercoupling all of the components, e.g., the battery to the switch and the LED, the USB-C port to the battery, the RCA jack to the ends of wire 2, etc.

All of the afore-described electrical components of the biotransducer may be arranged longitudinally with the cylindrical housing in the order seen in FIG. 1. That is, the end cap 6 in contact with the battery 5 at the rear, followed by the LED 3, and then the wire wrapped crystal 1. A transparent covering 8 (see FIG. 5) may be positioned over the front end of the housing through which the therapeutic light can emanate to be applied to a body or body part. The transparent covering 8 may be a lens and may be constructed of glass, polycarbonate, or any other suitable material. The cylindrical housing 7 may be sized of a diameter that snugly fits the cylindrical battery 5. The LED light 3 may be fitted with a heat sink 4 to dissipate heat from the light source. The heat sink 4 may be cylindrical and may be sized and shaped to fit snuggly within the housing so as to hold itself and the LED 3 in a fixed position within the housing 7.

Additionally, the crystal may be fitted with one or more pliable annular bushings 11 fitted at opposite ends of the middle segment 1b of the crystal. Each of bushings 11 may have an inner diameter sized to snuggly fit over the cylindrical middle segment of the crystal 1 in a relatively tight and fixed manner, and an outer diameter sized to snuggly mate with the inner diameter of the housing 7 in order to relatively tightly hold the crystal in a fixed position within the housing. The bushings 11 may also serve to trap the coil 2 in position around the middle segment of the crystal, i.e., trapped between the inner surface of the housing 7, the outer surface of the middle segment 1c of the crystal 1, and the two bushings 11.

As previously mentioned, in operation, an external frequency generator unit is coupled to the wire 2 of the biotransducer through the jack 6b to supply a specific electrical signal thereto that generates an electromagnetic field via the interaction of the coiled wire 2 and the piezoelectric crystal 1. The light from the LED 3 is passed through the crystal and the aforementioned electromagnetic field, and then out through the lens 8 to be applied to the body or body part being treated.

Figure 5:
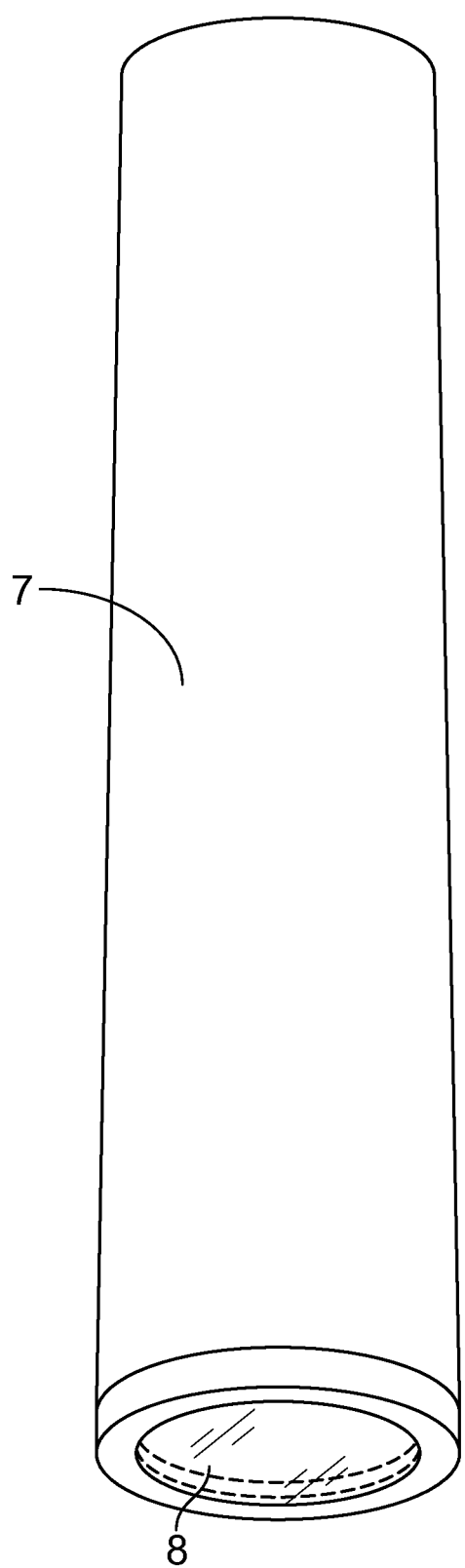
FIG. 5 is a pictorial of a fully assembled biotransducer in accordance with an embodiment.

FIG. 5 is a diagram of the assembled biotransducer. As can be seen, the light that emanates from the LED that passes through the crystal and electromagnetic field, then passes through the lens/covering 8 and out of the biotransducer. The light output of the biotransducer is pointed at the body part to be treated to shine the light upon the body part.

Each of (1) the wavelength of the light, (2) the electrical signal applied to the wire coil, and (3) the shape, size, and other characteristics of the piezoelectric crystal influences the therapeutic effect of the treatment. Each of these parameters may be varied as a function of the therapeutic effect desired and the body or body part being treated in accordance with the principles of cellular voltage mentioned above and in other reference sources.

CONCLUSION

Although features and elements are provided above in particular combinations, one of ordinary skill in the art will appreciate that each feature or element can be used alone or in any combination with the other features and elements. The present disclosure is not to be limited in terms of the particular embodiments described in this application, which are intended as illustrations of various aspects. Many modifications and variations may be made without departing from its spirit and scope, as will be apparent to those skilled in the art. No element, act, or instruction used in the description of the present application should be construed as critical or essential to the invention unless explicitly provided as such. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods or systems.

It is also to be understood that the terminology used herein is for the purpose of describing particular embodiments only, and is not intended to be limiting.

In addition, the methods provided herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, MME, EPC, AMF, or any host computer.

Variations of the method, apparatus and system provided above are possible without departing from the scope of the invention. In view of the wide variety of embodiments that can be applied, it should be understood that the illustrated embodiments are examples only, and should not be taken as limiting the scope of the following claims. For instance, the embodiments provided herein include handheld devices, which may include or be utilized with any appropriate voltage source, such as a battery and the like, providing any appropriate voltage.

Moreover, in the embodiments provided above, processing platforms, computing systems, controllers, and other devices that include processors are noted. These devices may include at least one Central Processing Unit ("CPU") and memory. In accordance with the practices of persons skilled in the art of computer programming, reference to acts and symbolic representations of operations or instructions may be performed by the various CPUs and memories. Such acts and operations or instructions may be referred to as being "executed," "computer executed" or "CPU executed."

One of ordinary skill in the art will appreciate that the acts and symbolically represented operations or instructions include the manipulation of electrical signals by the CPU. An electrical system represents data bits that can cause a resulting transformation or reduction of the electrical signals and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to or representative of the data bits. It should be understood that the embodiments are not limited to the above-mentioned platforms or CPUs and that other platforms and CPUs may support the provided methods.

The data bits may also be maintained on a computer readable medium including magnetic disks, optical disks, and any other volatile (e.g., Random Access Memory (RAM)) or non-volatile (e.g., Read-Only Memory (ROM)) mass storage system readable by the CPU. The computer readable medium may include cooperating or interconnected computer readable medium, which exist exclusively on the processing system or are distributed among multiple interconnected processing systems that may be local or remote to the processing system. It should be understood that the embodiments are not limited to the above-mentioned memories and that other platforms and memories may support the provided methods.

In an illustrative embodiment, any of the operations, processes, etc. described herein may be implemented as computer-readable instructions stored on a computer-readable medium. The computer-readable instructions may be executed by a processor of a mobile unit, a network element, and/or any other computing device.

There is little distinction left between hardware and software implementations of aspects of systems. The use of hardware or software is generally (but not always, in that in certain contexts the choice between hardware and software may become significant) a design choice representing cost versus efficiency tradeoffs. There may be various vehicles by which processes and/or systems and/or other technologies described herein may be effected (e.g., hardware, software, and/or firmware), and the preferred vehicle may vary with the context in which the processes and/or systems and/or other technologies are deployed. For example, if an implementer determines that speed and accuracy are paramount, the implementer may opt for a mainly hardware and/or firmware vehicle. If flexibility is paramount, the implementer may opt for a mainly software implementation. Alternatively, the implementer may opt for some combination of hardware, software, and/or firmware.

The foregoing detailed description may have set forth various embodiments of the devices and/or processes via the use of block diagrams, flowcharts, and/or examples. Insofar as such block diagrams, flowcharts, and/or examples include one or more functions and/or operations, it will be understood by those within the art that each function and/or operation within such block diagrams, flowcharts, or examples may be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), and/or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein may be distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc., and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system may generally include one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity, control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components included within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality may be achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, where only one item is intended, the term "single" or similar language may be used. As an aid to understanding, the following appended claims and/or the descriptions herein may include usage of the introductory phrases "at least one" and "one or more" to introduce claim recitations. However, the use of such phrases should not be construed to imply that the introduction of a claim recitation by the indefinite articles "a" or "an" limits any particular claim including such introduced claim recitation to embodiments including only one such recitation, even when the same claim includes the introductory phrases "one or more" or "at least one" and indefinite articles such as "a" or "an" (e.g., "a" and/or "an" should be interpreted to mean "at least one" or "one or more"). The same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items. Moreover, as used herein, the term "set" is intended to include any number of items, including zero. Additionally, as used herein, the term "number" is intended to include any number, including zero. And the term "multiple", as used herein, is intended to be synonymous with "a plurality".

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like includes the number recited and refers to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Moreover, the claims should not be read as limited to the provided order or elements unless stated to that effect. In addition, use of the terms "means for" in any claim is intended to invoke 35 U.S.C. § 112, ¶6 or means-plus-function claim format, and any claim without the terms "means for" is not so intended.

Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs). Application Specific Standard Products (ASSPs); Field Programmable Gate Arrays (FPGAs) circuits, any other type of integrated circuit (IC), and/or a state machine.

In addition, although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A biotransducer for treating medical ailments comprising:
 a resonant circuit comprising an inductor and a piezoelectric crystal;

a light source for producing illumination, wherein the light source is positioned relative to the resonant circuit such that illumination emanating from the light source passes through an electromagnetic field of the resonant circuit;

wherein the piezoelectric crystal comprises a unitary body having a first longitudinal segment at a first end thereof, a second longitudinal segment in the middle thereof, and a third longitudinal segment at a second end thereof, wherein the second longitudinal segment is cylindrical, the first longitudinal segment is tapered away from the second longitudinal segment to a first point, and the third longitudinal segment is tapered away from the second longitudinal segment to a second point, wherein the taper angle of the first longitudinal segment is 63 degrees and the taper angle of the second longitudinal segment is 54 degrees; and wherein the light source is positioned relative to the resonant circuit such that illumination emanating from the light source passes through an electromagnetic field of the resonant circuit from the direction of the first point to the second point of the piezoelectric crystal.

2. The biotransducer of claim 1 wherein the inductor comprises an electrically conductive wire folded over upon itself and wrapped around the piezoelectric crystal.

3. The biotransducer of claim 2 wherein the folded over wire comprises one continuous wire having a fold point where the wire is folded upon itself to form a first wire segment emanating from the fold point and a second wire segment emanating from the fold point, and wherein the first and second wire segments are twisted around each other at a 45 degree angle.

4. The biotransducer of claim 3 wherein the folded over wire is wrapped around the second longitudinal segment of the piezoelectric crystal.

5. The biotransducer of claim 3 wherein the crystal is quartz.

6. The biotransducer of claim 3 wherein the crystal is 76 mm in length, and wherein the first longitudinal segment is 23 mm, the second longitudinal segment is 23 mm, and the third longitudinal segment is 29 mm.

7. The biotransducer of claim 6 wherein the crystal comprises 24 facets and the second longitudinal segment is 29 mm in diameter measured from an edge of a facet to an edge of an opposing facet.

8. The biotransducer of claim 1 wherein the inductor is configured to be connected to a frequency generator circuit for applying electrical patterns to the inductor having therapeutic effect.

9. The biotransducer of claim 8 further comprising the frequency generator circuit.

10. A method of treating medical ailments, the method comprising:

transmitting light toward tissue through an electromagnetic field generated by a resonant circuit comprising an inductor and a piezoelectric crystal while applying an electrical signal pattern to the resonant circuit;

wherein the piezoelectric crystal comprises a unitary body having a first longitudinal segment at a first end thereof, a second longitudinal segment in the middle thereof, and a third longitudinal segment at a second end thereof, wherein the second longitudinal segment is cylindrical, the first longitudinal segment is tapered away from the second longitudinal segment to a first point, and the third longitudinal segment is tapered away from the second longitudinal segment to a second point, wherein the taper angle of the first longitudinal segment is 63 degrees and the taper angle of the second longitudinal segment is 54 degrees.

11. The method of claim 10 wherein the light passes through the piezoelectric crystal longitudinally from the direction of the first point to the second point of the piezoelectric crystal.

12. The method of claim 11 wherein the inductor comprises an electrically conductive wire having a first end and a second end, the wire folded over upon itself and wrapped around the piezoelectric crystal.

13. The method of claim 10 wherein the applying the electrical signal pattern to the resonant circuit comprises applying the electrical signal across the first end and the second end of the wire.

14. The method of claim 12 wherein the folded over wire comprises one continuous wire having a fold point where the wire is folded upon itself to form a first wire segment emanating from the fold point and a second wire segment emanating from the fold point, and wherein the first and second wire segments are twisted around each other at a 45 degree angle.

15. The method of claim 14 wherein the crystal is quartz.

16. The method of claim 14 wherein the crystal is 76 mm in length, and wherein the first longitudinal segment is 23 mm, the second longitudinal segment is 23 mm, and the third longitudinal segment is 29 mm.

17. The method of claim 16 wherein the crystal comprises 24 facets and the second longitudinal segment is 29 mm in diameter measured from an edge of a facet to an edge of an opposing facet.

* * * * *